United States Patent [19]

Blum

[11] 4,264,327
[45] Apr. 28, 1981

[54] METHOD AND APPARATUS FOR AUTOMATIC COMPETITIVE BINDING ANALYSIS

[76] Inventor: Alvin S. Blum, 2350 Del Mar Pl., Fort Lauderdale, Fla. 33301

[21] Appl. No.: 898,998

[22] Filed: Apr. 21, 1978

[51] Int. Cl.³ .................... G01N 33/56; G01N 35/08
[52] U.S. Cl. .................................. 23/230 B; 23/920; 422/81; 422/82; 204/180 G; 435/291
[58] Field of Search ............... 23/230 R, 230 B, 920; 422/81, 82, 71; 356/197; 204/180 G; 435/291

[56] References Cited

U.S. PATENT DOCUMENTS

| | | | |
|---|---|---|---|
| 3,320,148 | 5/1967 | Skeggs | 422/82 |
| 3,320,149 | 5/1967 | Isreeli | 422/82 |
| 4,009,005 | 2/1977 | Johnson | 422/71 |
| 4,128,628 | 12/1978 | Brooker | 422/71 |
| 4,141,687 | 2/1979 | Forrest et al. | 422/82 |
| 4,153,416 | 5/1979 | Bonner et al. | 422/71 |

*Primary Examiner*—Ronald Serwin

[57] ABSTRACT

Automatic continuous competitive binding analyzer comprising: controlled combination and incubation of ligand, labeled ligand, and ligand specific binding agent; isolation of serial samples by spacer fluid; light absorbing agent for identifying portions of stream; light activated fluid control directing fluid flow and processing; separation of bound ligand from unbound ligand; novel electroextraction for separating certain molecules in flowing stream; serially introducing separated portions of stream into label measuring device. Use of a plurality of static detectors to reduce average processing time below radioactivity measurement time when label is radioactive.

56 Claims, 17 Drawing Figures

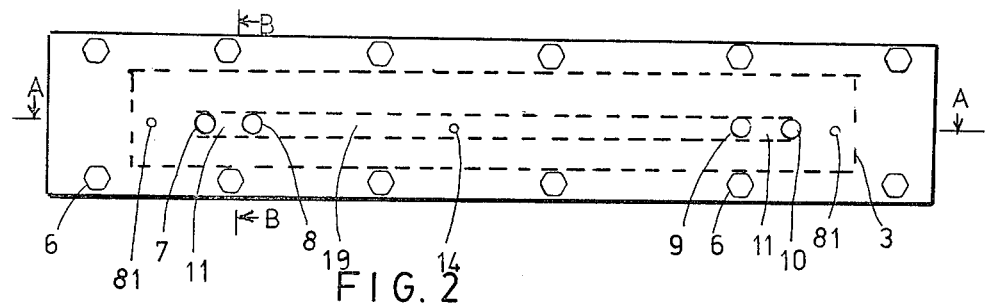
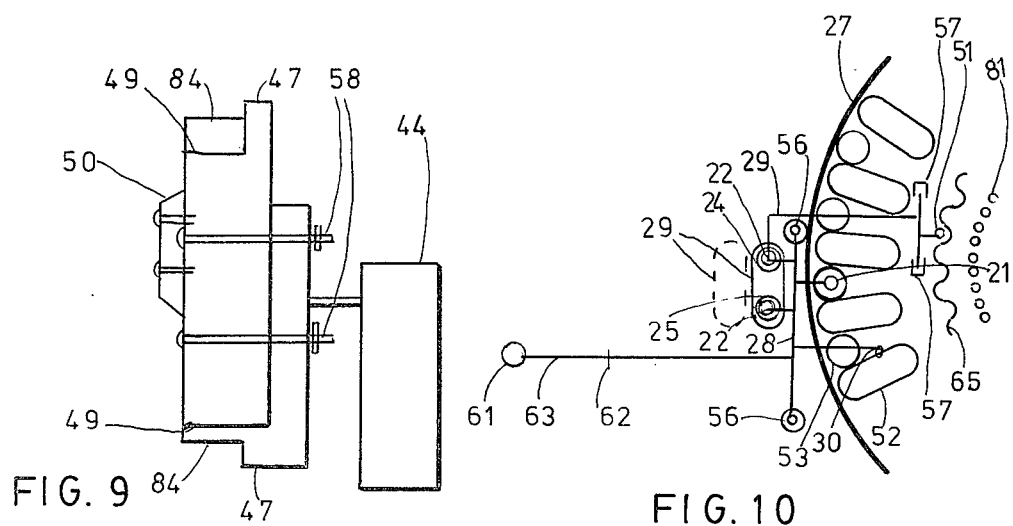
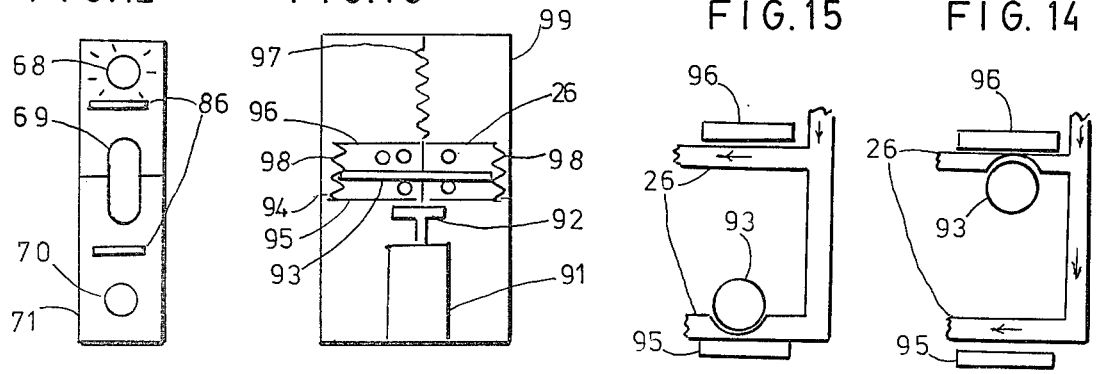

METHOD AND APPARATUS FOR AUTOMATIC COMPETITIVE BINDING ANALYSIS

BACKGROUND OF THE INVENTION

1. Field of the Invention

The invention relates to a method and apparatus for analyzing the concentration of a substance in a sample liquid by the technique of competitive binding analysis, a currently important subdivision of which is radioimmunoassay. The technique involves the combining of the substance to be measured (ligand) with a specific binding agent. The ligand is often an antigen and the binding agent an antibody thereto. The extend of the reaction is measured by a label or tracer, usually radioactive, but tracer may also be, for example, fluorescent or an enzyme. The present innvention relates in particular to methods and apparatus permitting such analysis to be made more rapidly by machine with a minimum of labor and error.

2. Description of the Prior Art

Yalow and Berson (Nature 1 84,1648,1959) introduced a new analytical method for assaying the minute amounts of insulin found in the blood. An antibody to insulin was mixed with the sample plus a known amount of radioactive insulin. The total concentration of insulin exceeded the binding capacity of the antibody. At equilibrium, when all the antibody was bound to either radioactive insulin or nonradioactive insulin, the antibody bound insulin was separated from the free insulin by membrane electrophoresis and the radioactivity in each portion measured. By means of standards a relationship was established between the ratio of bound to unbound radioactivity and the amount of insulin in the sample. Because the general analytical principle of the method is so exquisitely sensitive and specific for biologically important molecules that are difficult to analyze by other means, the method has grown and diversified into an important clinical procedure.

Specific binding agents now include cell membrane receptors, tissue receptors, naturaly occurring specific binding agents such as the transins as well as the more common antibodies.

Ligands include elements, peptide hormones, steroid hormones, proteins, virus and tumor components. In addition to radioactive labeling we also find fluorescent and other optical labels and enzyme labeling. In those cases where the binding agent is the analyte, a constant amount of ligand is employed.

Separation methods include: differential migration of bound and unbound ligand such as gel filtration, chromatography, zone electrophoresis; isolation of unbound ligand by adsorbtion on coated charcoal, silica, talc; isolation of bound ligand by double antibody precipitation, salt precipitation, ethanol precipitation, dialysis. The Skeggs (U.S. Pat. No. 2,797,149) continuous dialysis and the Ferrari (U.S. Pat. No. 3,211,645) continuous filtration techniques have not been employed for this separation. Solid phase systems employing binding agent affixed to test tube wall, beads or column packing have become popular.

Because of the increase in the volume and applications of this technique to clinical medicine, recent attention in this area has centered an automatic and semiautomatic systems for performing these analyses. Many of these are adaptations of the continuous chemical analyzer of Skeggs (U.S. Pat. No. 2,797,149). These include the devices marketed by Technicon Corp. which use magnetic retention of iron coupled antibody. Also the Brooker (U.S. Pat. No. 4,022,577) method of dynamic measurement of total radioactivity followed by a second static measurement of one separated component. Also the Johnson (U.S. Pat. No. 3,896,217) method of separation with alternate adsorbtion and elution of one component on a column containing antibody fixed to the column making for efficient reutilization of antibody. A need exists for a technique which combines automation with simplicity, versatility and greater throughput rate for samples.

SUMMARY OF THE PRESENT INVENTION

One object of the present invention is to provide an automatic and continuous assay method for the rapid and accurate determination of ligand or binder through specific ligand binder interaction using a novel technique for separation of bound ligand from unbound ligand. An advantage of the separation means lies in its ability to retain gas bubbles in the liquid stream which reduce carryover at high throughput rates.

Another object of the present invention is to provide an automatic and continuous assay method and apparatus for the accurate quantitation of ligand or binder through specific ligand binder interaction using a novel liquid pathway control means.

Another object of the present invention is to provide an apparatus and method for automatic assay of binder or ligand by competitive binding analysis providing liquid spacer means for isolating a series of sample mixtures from each other and a light absorbing constituent in the mixture or spacer fluid to provide a signal for liquid pathway control means.

Optical detector means sense said light absorbing costituent. Liquid pathway control means are actuated by said optical detector means. This method makes it possible to distinguish between sample mixture and spacer fluid automatically for such purposes as washing columns when a column separation method is used. More especially it provides means to position correct portion of liquid stream in one or a plurality of label measurement devices or test tubes for later label measurement.

These and other objects of the present invention as will become apparent can be attained by the use of a method and apparatus wherein a precise amount of a solution of a known concentration of ligand, labeled, for example, with a radioactive isotope, and a solution containing a known concentration of binding agent is admixed with the sample solution containing either a known (standards for calibration) or unknown concentration of ligand to be measured which is reactable with said binding agent. The concentration of binding agent is so selected as to be insufficient to react with all the ligand present. This is true except in the special case wherein the analyte is the binding agent. In that case a fixed concentration of labeled ligand in excess of the expected amount of binding agent is employed. The mixture is permitted to incubate for a fixed time interval. The incubated mixture is then separated into bound ligand fraction and unbound ligand fraction by separation means. One of these fractions is then directed to label measurement means where radioactivity is measured and recorded. A complication of radioactivity measurement is that definite time (usually one minute) is required to perform a statistically reliable measurement. It is therefore desirable to perform a static rather than a dynamic measurement thereof This has limited the throughput rate of previous automatic systems to less than one sample per minute. The liquid control means of the present invention overcomes this limitation.

In a continuous chemical analyzer, when a series of samples are sequentially introduced into a liquid stream, Skeggs and Techicon Corp. demonstrated and they may be spaced and separated from one another by the introduction of a wash or spacer liquid between each sample and multiple air bubbles segmenting the liquid stream without the likelihood of mixing such samples and with the aid of which samples of different characteristics may be analyzed continuously, one after another at brief intervals. One improvement of the present invention results from the introduction of a light absorbing material into either the sample mixture or the spacer liquid for control of operation. The presence of the light absorbing material is sensed by an in line optical detector. This in turn operates control means to perform required functions. Whe separation means is an adsorbtion column, control means provides large volumes of buffer to wash the column when sensing means indicates the column is between samples, i.e. spacer fluid is flowing. A novel function of the control means resolves the throughput limitation of earlier automatic radioimmunoassay devices imposed by the static radioactivity measurement interval. In a simple inexpensive embodiment, the separated stream from the separation means is lead to a two way liquid deflector or valve. One way directs flow to waste, the other to a multiple container filling turntable such as one of the automatic fraction collectors in common use. When spacer liquid reaches the valve, the liquid is discarded until a sample mixture reaches the valve, which, under signal from optical detector, diverts the liquid stream into a fresh empty container. Alternate discarding of spacer and filling of tubes with sample provides a set of filled tubes ready for radioactivity measurement in any one of the many automatic test tube radioactivity measurement devices (gamma counters) in common use. Samples may be processed rapadily independent of radioactivity measurement. Radioactivity in the test tubes may be measured by a plurality of automatic gamma counters. If each one measures at the rate of one per minute, the overall rate would be equal to the number of counters per minute. Test tubes and their handling are eliminated in another embodiment of the invention having one or a plurality of self contained radioactivity measurement means. A channel or coiled channel contains the sample liquid mixture within the sensitive volume of each radioactivity measurement means. The optical detector actuated valve means is a multiport valve which directs the liquid flow into each of the coils in turn. On signal from optical detector means that spacer liquid has reached the valve, it directs the flow through a coil. The previous sample in the coil is flushed out with spacer liquid and the next sample fills the coil. The subsequent appearance of spacer liquid indicates the coil is filled with sample. Flow is now directed to the next coil and the static measurement interval begins for the sample trapped in the coil. Measurement interval continuous for a time, usually one minute. If four coils and a four way valve are used, the system processes almost 4 sample per minute. Calibration means correct any nonuniformity of sensitivity. With self contained recording and data processing means, the system can provide direct output of quantitative results when standardized with known concentrations of analyte. When the system contains a single coil, a portion of the spacer liquid is used to flush the coil, and the balance is diverted to waste. The flow to waste begins when the coil is filled. This starts the counting interval. When the predetermined time interval is completed, the balance of the spacer liquid is directed to the coil where it flushes the old sample out before the next sample fills it. Bubble retention throughout measurement reduces carryover between samples.

Another object of the present invention is to provide novel method and apparatus for the separation of a large molecule in a continuously flowing stream and more particularly bound ligand from unbound ligand while retaining the bubble separation means of Skeggs. Ligands are generally small molecules of molecular weight several hundred or less. Binding agents are generally large in size with molecular weights of tens of thousands or more. They often also have a smaller electrical charge to mass ratio. Consequently, after incubation of ligand and binding agent, we find two kinds of ligand, a small charged form and a very large form with lesser charge. This invention provides novel apparatus of simple and inexpensive construction to separate these two forms which comprises: a central channel through which flows the mixture of bound and unbound ligand; at least one additional parallel recipient flow channel adjacent the central channel and separated therefrom along its length by a semipermeable membrane of sufficient permeability to allow passage of the unbound ligand. The membrane need not be completely impermeable to the bound ligand. Electrodes in at least two of the channels with electric potential applied thereto. The electric potential applies a driving force to the charged molecules or ions. The unbound ligand with a greater charge to mass ratio than the bound ligand, experiences a greater driving force across the membrane. Being of much smaller size it moves through the solution more rapidly. Being of much smaller size, it passes through the semipermeable membrane more readily. The combination of all of these factors favors the movement of the unbound ligand over the bound ligand from the central channel to the recipient channel, resulting in the separation of the bound ligand in the central channel and the unbound ligand in the recipient channel. The extent of the separation will be influenced by the distance the unbound ligand must travel to reach the recipient stream. In a preferred embodiment a very thin, less than one millimeter, central channel is sandwiched between two parallel contiguous channels and separated therefrom by two semipermeable membranes. Each of the recipient channels contains an electrode. The electric field extends from the first recipient channel, across the first membrane, across the smallest dimension of the central channel, across the second membrane, to the electrode in the second recipient channel. All of the charged particles will tend to move out of the central channel in response to the electric field. A loss of ions may alter the composition of the incubated mixture unfavorably. For example, the ionic strength or acidity may change so much that ligand binding may be disrupted. By providing an ion containing stream on either side of the central channel, a charged particle from one recipient channel will tend to enter the central channel for every particle of like charge which leaves the central channel to the opposite recipient channel. This tends to stabilize the composition of the central channel. The flow rate through the recipient channels may be much greater than through the central to provide a surplus of ions and to wash away received ligand that has moved across by electric forces or by dialysis. In some cases dialysis may provide a considerable portion of the separation, it takes place independent of the electric forces. The length of said central channel is very great relative to the distance across said membranes so that the unbound ligand is exposed to the electric force for a prolonged period and the distance it must migrate for separation is very short.

The present invention provides a new composition of matter for those cases where the difference in size and charge of the bound and unbound ligand might not ordinarily be sufficient for separation by this electrical means. The binding agent is modified by combining it with a very large, inert, relatively uncharged soluble molecule. An example is the analysis of a protein ligand such as a hemoglobin variant by a specific antibody thereto. Both the hemoglobin and antibody are large protein molecules with molecular weights of 68,000 and 160,000 respectively with similar charge characteristics so that ligand and bound ligand are not readily separated by this method. The present invention provides a new form of binding agent by chemically combining the hemoglobin antibody with, for example, Dextran T-2000 an inert, low charge, water soluble polysaccharide with molecular weight of 2,000,000. An even more convenient binding agent modification includes the light absorbing property. For example the hemoglobin antibody may be chemically combined with Blue Dextran 2000, an inert, low charge, water soluble polysaccharide with molecular weight of 2,000,000 that is strongly light absorbing.

The foregoing and other objects of the present invention will be described more fully in the following more detailed description of the invention.

The two solutions, labeled ligand and binding agent and the liquid samples being analyzed are ordinarily stored in separate containers until ready for mixing. In order to conserve sample and reagents and to minimize carryover between samples, it is an object of the present invention that the pipet tips moves vertically and promptly from the liquids being aspirated at the conclusion of the sampling interval. It is a further object that these tips then be promptly immersed in wash or spacer liquid until the next sampling interval. It is a further object that the tips be promptly removed from the spacer liquid and then be immersed in the reagents and the next sample for the subsequent sampling interval. Liquid sampler apparatus are known and are disclosed in U.S. Pat. Nos. 3,902,371; 3,038,340; 3,424,557; 3,134,263; 3,230,776. It is an object of the present invention to provide a novel sampling apparatus of extremely simple and inexpensive construction better suited to the required function. The device consists of a pipet carrier means for liquid aspirating pipets (usually 3) that has only an up and down motion with three levels, and vertical motion means connected thereto. At the uppermost level, the pipet tips are raised high enough to clear the tops of the liquid containers so that the containers may move into and out of alignment with the tips without impediment. At this level, the flexible tubes connected to the pipet tips may be occluded by simple pinching off means. This draws a vacuum in the pump tubing which may be used later to aspirate liquid upon reimmersion. At the second, or middle level, the pipet tips are immersed in sample liquid and the two reagent solutions. When labeled ligand and binding agent are combined prior to analysis only one reagent container and reagent pipet are required. This level is very simply determined by a level sensing means rigidly fixed to the pipet carrier means which impinges on the sample carrier means. The third and lowest level position of the pipet tips is beneath the plane of the bottoms of the sample and reagent containers. The wash or spacer the bottoms of the sample nd reagent containers. The wash or spacer liquid containers or container are located at this lower level and the pipet tips are immersed therein. The level sensing means passes through an opening in the sample carrier means to descend to this third level. At this time in the cycle, the reagent carriers are displaced laterally, out of the pipet pathway. The sample carrier is in a position such that the sample pipet passes through an opening in the sample carrier means between two sample containers. The reagent container carrier performs a simple to and fro motion being under and aligned with the reagent pipet in one position, and adjacent to the pipet in the second position. The sample carrier motion may be either rotary or translatory. This motion is such that it presents a series of sample containers seriatim to the sampling pipet, with an intermediate position substantially midway between each of said containers with an opening in the carrier at each of these intermediate locations through which the sampling pipet penetrates to the lowest level at which it finds the spacer liquid. Drive means to impart motion to sample carrier, pipet carrier, and reagent carrier. Alternatively, cam means to impart lateral motion to reagent carrier may form part of the sample carrier.

BRIEF DESCRIPTION OF THE DRAWINGS

FIG. 2 is a top plan view of the electric separation apparatus.

FIG. 9 is a side view of the cam of FIG. 6.

FIG. 10 is a plan view of an embodiment of the sampler wherein pipet motion, sample carrier motion and reagent carrier motion are each provided by separate means.

FIG. 11 is a diagrammatic side view of the apparatus of FIG. 10.

FIG. 12 is a diagram of the optical detector.

FIG. 13 is a diagrammatic end view of novel two position valve means with the mechanism between the two operating positions.

FIG. 14 is a diagrammatic side view of the fluid flow directing means of FIG. 13 in the first position.

FIG. 15 is a diagrammatic side view of the fluid flow directing means of FIG. 13 in the second position.

Figure 1:
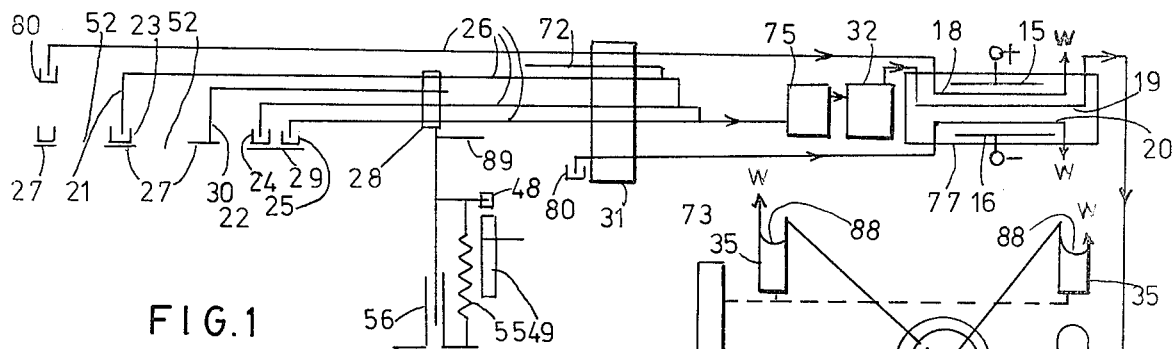
FIG. 1 is a schematic drawing of apparatus of the type to which the invention relates showing sampling module in the middle level position, embodying the electric separation means and multiple radioactivity measuring means on line.

The clarify the description, a list of items referred to by number in the drawings follows:

| | |
|---|---|
| W. waste | |
| 1. upper member | 11. bridge |
| 2. upper membrane | 12. lower recipient inlet |
| 3. center member | 13. lower recipient outlet |
| 4. lower membrane | 14. positive wire |
| 5. lower member | 15. upper electrode |
| 6. bolt | 16. lower electrode |
| 7. reagent mixture inlet | 17. negative wire |
| 8. upper recipient inlet | 18. upper channel |
| 9. upper recipient outlet | 19. center channel |
| 10. reagent mixture outlet | 20. lower channel |
| 21. sample pipet | 61. solenoid |
| 22. reagent pipet | 62. fulcrum |
| 23. sample | 63. lever |
| 24. ligand | 64. level microswitch |
| 25. binding agent | 65. turntable cam |
| 26. pump tubing | 66. step microswitch |
| 27. sample support | 67. gear microswitch |
| 28. pipet support | 68. light source |
| 29. reagent support | 69. fluid channel |
| 30. level sensing finger | 70. light sensor |
| 31. pump | 71. light shield |
| 32. incubator | 72. air line |
| 33. optical detector means | 73. confluent line |
| 34. 4 position rotary valve | 74. wash liquid container |
| 35. radioactivity measuring means | 75. mixer |
| 36. data processor and recorder | 76. incubator |
| 37. 2 way recirculate valve | 77. electric separator |
| 38. 1 way vent valve | 78. adsorbtion column |
| 39. 2 position tube mover | 79. column packing |
| 40. drop deflector | 80. recipient liquid container |
| 41. specimen test tube | 81. locator pin |
| 42. test tube turntable | 82. hole in center member |
| 43. stepping motor | 83. 2 way fluid diversion valve |
| 44. timing motor | 84. elevation on pipet support cam |
| 45. 3 way cam | 85. time switch |
| 46. ring gear | 86. light filter |
| 47. gear tooth part of cam | 87. detent holes |
| 48. pipet support cam follower | 88. coiled channel |
| 49. pipet lifting part of cam | 89. compression bar on pipet support |
| 50. reagent support part of cam | 90. turntable bearing |
| 51. reagent support cam follower | 91. solenoid coil |
| 52. hole through sample support | 92. solenoid armature |
| 53. sample receptacle | 93. armature extension bar |
| 54. reagent support spring | 94. stop |
| 55. pipet support spring | 95. lower spring loaded anvil |
| 56. sliding sleeve bearing | 96. upper fixed anvil |
| 57. rotary bearing | 97. armature return spring |
| 58. clamp screw | 98. lower anvil spring |
| 59. anvil | 99. housing |
| 60. compression spring | |

DESCRIPTION OF THE PREFERRED EMBODIMENT

Figure 1A:
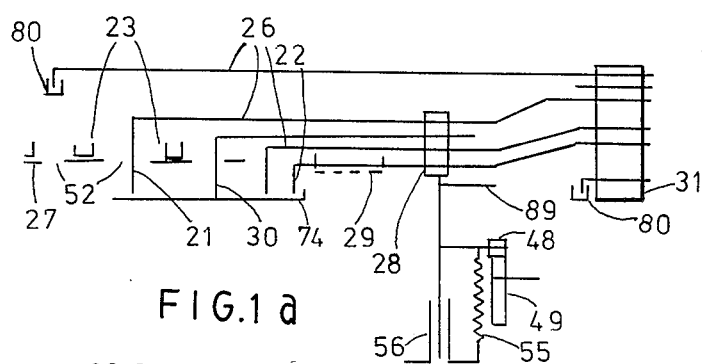
FIG. 1a is a diagram of sampler in the lower level or wash position.
Figure 1B:
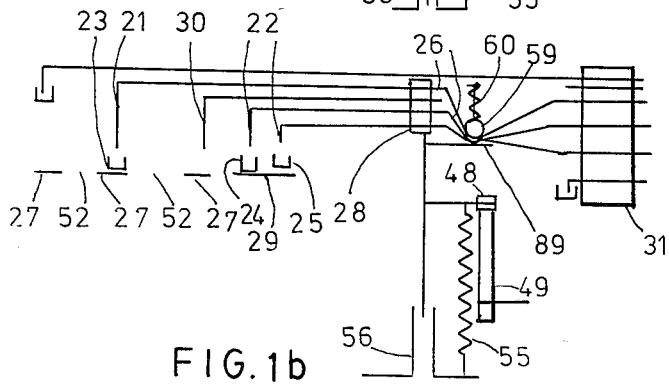
FIG. 1b is a diagram of sampler in the uppermost or clearance position showing pinching means for occluding pipet tubing.

Referring first to FIG. 1, competitive binding analysis is carried out by the addition of labeled ligand 24 and specific binding agent 25 to each sample or standard 23. Peristaltic proportioning pump 31 pulls fluid at precise rates through flexible tubing lines 26, metering the fluids. Three of these lines terminate in sample pipet 21 and two reagent pipets 22. Pipet support means 28 holds these three pipets in position such that they are immersed in their respective liquids for a precise time interval. Level sensing finger 30 is fixed to support 28. This rests upon sample support means 27 and prevents pipets being pulled to a lower level by tension spring 55. This defines the middle of three levels at which pipets operate. A second operating position of pipets is shown in FIG. 1a. Rotation or translation of sample support 27 has aligned hole 52 in the support with level sensing finger 30 allowing it to penetrate. Spring 55 pulls pipet support 28 to a lower level at which cam follower 48 inpinges on surface of drive cam 49. In this position, sample pipet 21 passes through a hole 52 between samples in sample support 27. Sample pipet 21 and reagent pipets 22 are now immersed in and aspirating wash or spacer liquid from wash liquid container 74 at a level beneath sample and reagent level. Reagents 24 and 25 have been displaced laterally out of the way of pipets 22 by movement of reagent support 29. FIG 1b shows the third operating level of the pipets when cam 49 forces cam follower 48 and pipet support 28 to such a high level that the pipet tips clear the tops of the sample and reagent containers while these containers move. In this clearance position, compression bar 89 on pipet support 28 forces flexible tubes 26 against anvil 59 compressing springs 60 and pinching the tubes 26 closed. Occlusion of tubes causes vacuum to form in pump lines. When pipets are abruptly returned to liquid by action of spring 55, a rapid liquid flow occurs until vacuum is dissipated. This reduces volume of air aspirated into liquid lines during sample changing and increases throughput. Returning to FIG. 1, the three liquid streams are joined by a fourth fluid stream pumping gas, usually air. The air is introduced via line 72 and flows with liquids into confluent line 73 to mixer 75 and incubator 32. Mixer 75 usually consists of a coiled tube with the coils running vertically. The incubator is an elongate coiled tube that may be surrounded by a controlled temperature. The air introduced concomitantly with the flow of liquids divides the fluid stream into a segmented fluid stream composed of alternate segments of liquid and air. In the course of travel of this stream, the segments of air and the surface tension of the air/liquid interfaces displace liquid from the inner surface of the tube or other fluid channel so as to prevent or substantially reduce the mixing of the samples with each other and hence prevent or reduce the contamination of one sample by another in the operation of the machine for analyzing a series of samples or standards. After thorough mixing of the three liquids and incubation to allow time for binding agent to combine at least partially with labeled and unlabeled ligand, the stream passes to separation module 77 and FIG. 3 where free ligand will be removed from the stream leaving the bound ligand in the stream for subsequent measurement. It should be noted that the dynamic, continuous nature and precise, reproducible timing of this system allow analysis with incomplete reaction of ligand and binding agent. When standards and unknowns receive identical treatment, the separation step may be performed many hours before equilibrium is reached and yield valid results. Incubated, segmented liquid stream enters central channel 19 of separator 77. Recipient liquid streams are pumped from containers 80 through upper channel 18 and lower channel 20. A difference of electric potential is applied between electrodes 15 and 16 within channels 18 and 20 respectively. Materials with net positive change are accelerated toward cathode 16 in lower channel and materials with net negative charge are accelerated toward anode 15 in upper channel. Small molecules will move faster than large molecules. Highly charged molecules will move faster than lesser charged molecules. The semipermeable membranes 2 and 4 separating channel 19 from channels 18 and 20 are selected of a pore size to allow ready passage of the smaller unbound ligand and may retard passage of the larger, bound ligand. Millipore Filter Corp. markets a selection of suitable membrances with a choice of pore sizes. By pumping much greater volumes of liquid through recipient channels, unbound ligand reaching recipient channels is swept away before it can diffuse back into central channel. The recipient streams provide a surplus of ions to replace any lost from the central channel. This tends to maintain the acidity and ionic strength of the mixture within the central channel. It is important to avoid perturbation of its composition that might alter the binding phenomena. Recipient liquid streams leaving separator at outlets 9 and 13 are sent to waste w. Liquid in central channel, divested of its unbound ligand is now forced through optical detector 33 into four position rotary valve 34. A light absorbing agent of such nature as to remain within the central channel, is added to either one of the reagents or the wash liquid. The light absorbing agent may be fluorescent, in which case the emitted light may be detected. A large molecular weight, low net charge, water soluble, inert compound such as Blue Dextran 2000, a product of Pharmacia Fine Chemicals Corp., may be used. The system will operate with the color in either reagent or wash stream with a simple change is switching signals. The colored agent may be chemically incorporated into the binding agent. This has the added advantage of increasing the difference in size and charge between bound and unbound ligand. The following describes operation when color is in reagent mixture. This will remain with bound ligand in the central channel and pass through optical detector 33. The optical detector senses the presence or absence of the colored agent. In this case it is wired to send a switching command to 4 position rotary valve 34 whenever the color of the solution disappears. To prevent false triggering by air segments, a time delay is built in, requiring continued absence of color for a time longer than an air segment would cause. Liquid flows into central port of valve and out of one of the four exit ports to a coil 88 in one of the four radioactivity measuring devices 35. A suitable electrically operated valve is marketed by the Hamilton Company. The time delay of the signal from the optical detector is set long enough for the interface between reagent and wash liquid to enter the coil 88 before the valve 34 switches. The coil 88 in radioactivity measuring device 35 is large enough so that the entire colored reagent segment is contained therein. Upon switching, the entire colored segment containing the bound labeled ligand is trapped within the sensitive volume of the measuring device for a static measurement for a fixed time interval which is initiated by the same signal. While the next coil in sequence is being flushed and filled, the measuring continues. At the end of the measuring interval, the accummulated measurement is transmitted to the data processor and recorder module 36 and the device 35 is reset and ready for the next refill. After 3 more reagent segments have been inserted in turn in the other coils, the valve will again switch to this coil and spacer fluid will first wash out the old specimen to waste until a new colored specimen fills and is trapped in the coil. The air segments in the measuring coils do not interfere with measurement. In continuous analysis, Habig, R. L. Clin. Chem. 15,1045,1969, demonstrated that retaining air segmentation throughout can reduce cross contamination to such an extent that throughput (samples/minutes) can be considerably increased. If a new sample or standard is picked up every fifteen seconds, this system allows measuring intervals of at least 55 seconds while maintaining a throughput of 4 samples/minute. The nature of radioactive analysis requires a static measurement of almost a minute. This has limited the throughput of many present automatic radioimmunoassay systems. The present invention overcomes this limitation by freeing the processing of specimens from the measurement of radioactivity. Prior to the analysis of samples and standards, four identical specimens would oridnarily be entered into the system. These would eventually fill the 4 measuring devices 35 and the results of their measurement would be entered in processor 36. Any differences in values can be used to correct subsequent data for inequalities in sensitivity of the four detectors. Processor 36 may contain a modest computer for making such correction, formulation of standard relationships and calculation of concentrations of samples.

Figure 3:
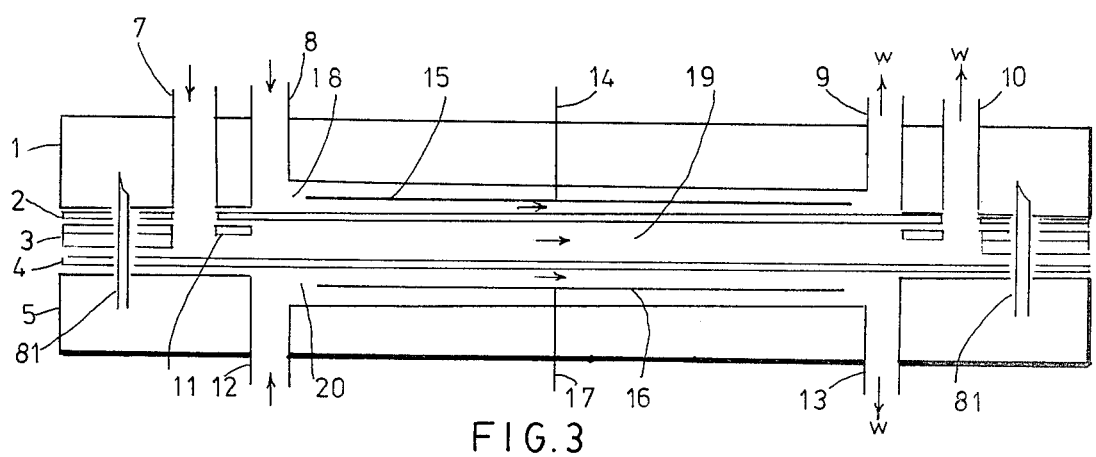
FIG. 3 is a sectional view, taken on line A—A of FIG. 2.
Figure 4:
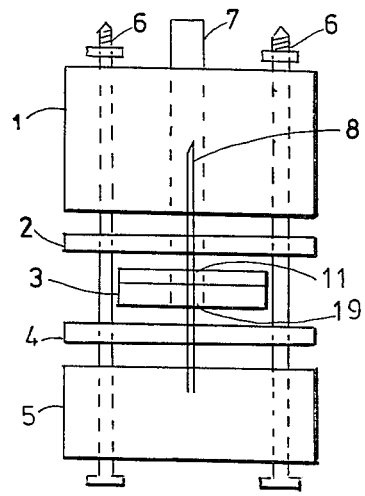
FIG. 4 is a sectional view, taken on line B—B' of FIG. 2.

FIG. 2 shows a plan view of an embodiment of the electric separation apparatus, FIG. 3 is a sectional view taken on line A—A' of FIG. 2 and FIG. 4 is a sectional view taken on line B—B' of FIG. 2. Rigid and thick upper member 1 and lower member 5 and thinner center member 3 are bolted together with bolts 6 sandwiching in thin semipermeable membranes 2 and 4. These drawings are not to scale. Center member 3 and membranes 2 and 4 are shown much thicker than they are for clarity. Upper member 1 has groove 18 on its underside terminating at tubes 8 and 9. Member 5 has groove 20 on its upper surface terminating in tubes 12 and 13. Center member 3 has slot 19 which connectes with tubes 7 and 10 in upper member 1 via 2 holes in membrane 2. When membranes 2 and 4 are tightly compressed by bolts 6, the grooves and slots are sealed so that three parallel channels are formed through which fluid may be passed. The central channel 19 terminates at reagent mixture inlet 7 and outlet 10. Membrane 2 forms a common wall that channel 19 shares with upper channel 18 and membrane 4 forms a common wall that channel 19 shares with lower channel 20. Upper channel 18 terminates in recipient inlet 8 and outlet 9. Lower channel 20 terminates in recipient inlet 12 and outlet 13. Electrode 15 in channel 18 and electrode 16 in channel 20 are connected to positive wire 14 and negative wire 17 respectively. The exact nature of the applied difference of potential may be varied to suit requirements. In the assembly of separator 77, sharp pointed locator pins 81, fastened to lower member 5 transfix membranes 2 and 4 and pass thru holes in upper and center members to facilitate alignment and hold componenents during assembly. Bolts 6 have sharpened points which pierce membranes during insertion to prevent membrane displacement. After bolting, holes are punched in membrane 2 thru inlet 7 and outlet 10. During operation of the separator it was noted that leakage occurred between recipient stream and reagent mixture stream where inlets 7 and 8 meet membrane 2. Construction of center member 3 was then modified to provide the 2 bridges 11 between inlets 7 and 8 and outlets 9 and 10. This was easily accomplished by constructing the center member of a top and a bottom piece laminated together. The bottom piece had a slot cut between holes in membrane at 7 and 10. The top piece had holes cut at 7 and 10 and a slot cut between 8 and 9, leaving bridges 11 to seal the membrane at these points. An air segmented mixture of bound and free ligand is forced thru cental channel 19 via tube 7 (arrows indicate fluid flow). Appropriate recipient fluids such as conductive buffers are passed thru channels 18 and 20 via tubes 8 and 12. a difference of electrical potential is applied to electrodes 15 and 16 via 14 and 17. Charged ligand will migrate toward one of the electrodes as the mixtures passes thru channel 19. Bound ligand will migrate more slowly than free ligand. Membranes will be selected of a porosity to be freely permeable to the small free ligand molecule but to stop or retard the very much larger bound ligand. Appropriate selection of voltage, pH, ionic strength and flow rate of solutions will regulate separation of free ligand from bound ligand so that bound ligand will emerge from tube 10 and free ligand from either tube 9 or 13. Either or all streams may then be collected for subsequent measurement or passed thru detectors for immediate measurement. This is but one embodiment of the invention. The channels may be formed in other ways or convoluted. There may be only a single membrane with one electrode within the donor stream, and one in the recipient stream. Two electrodes with two membranes allows the doner stream to gain as many charges as it loses, maintaining its composition and avoiding electrode effects. Air segmentation is maintained throughout.

Figure 5:
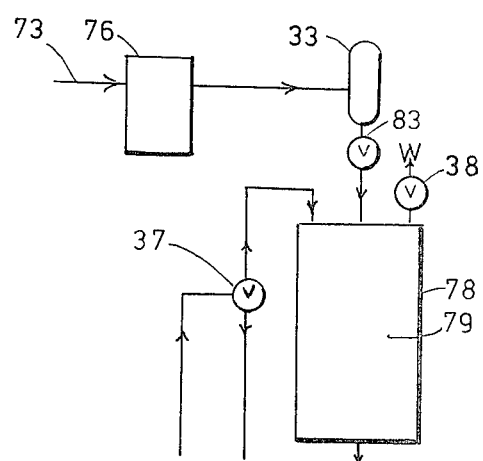
FIG. 5 is a schematic diagram of apparatus of the type to which the invention relates embodying two optical detectors, column adsorbtion separation means, and separated specimen collecting means for later radioactivity measurement off line.

FIG. 5 shows an embodiment of the present invention employing adsorbtion column means for separation of bound ligand from free ligand. One optical detector 33 controls fluid flow through the column. A second optical detector 33 independently controls a collector for collecting separated specimens for later radioactivity measurement by any of a number of independent automatic radioactivity measuring devices. After the air segmented, colored mixture is mixed in mixer 75 and incubated in incubator 76, it passes through the first optical detector 33 and into adsorbtion column 78 which may be packed with any one or several adsorbtive separating agents 78 such as were enumerated earlier for adsorbtion of either the bound ligand, or, more commonly, the unbound ligand which will be used in this example. First optical detector 33 closes one way vent valve 38 when spacer liquid arrives. Two way diversion valve 83 directs spacer stream to waste and 2 way recirculation valve 37 directs a large volume flow of eluting buffer through the column. When another bolus of reagent mixture appears at first optical detector, vent valve 38 opens to discharge air segments to atmosphere. Valve 83 directs reagent mixture through column. And valve 37 shunts rapid buffer flow back to buffer reservoir. An advantage of the adsorbtion column separation means is its versatility. It may be applied to the separation of a wide variety of ligands and binding agents without changing columns. It has the disadvantage that air segmentation is lost and flow within the column is slow and erratic so that some mixing and carryover of samples limits throughput. Copious quantities of eluting buffer helps overcome this difficulty. Independent of the above switching operations the second optical detector 33 is actuated by presence and absence of the colored bolus eluting from column 78. It operates 2 position tube mover 39 to position flexible column effluent tube 26 directly over specimen test tube 41. When colored reagent mix has all passed this optical detector and buffer liquid appears, the optical detector switches tube mover 39 to position outlet tube over waste reservoir and stepping motor 43 advances turntable 42 presenting a clean test tube for next separated specimen. Drop deflector 40 catches any drops during tube movement. When all the specimens have been collected, the test tubes are inserted in any of the many commercially available automatic gamma counters used for measuring the radioactivity in test tubes. There is a distinct economic advantage in incorporating this test tube collection means into an automatic competitive binding analyzer. Many of the laboratories that feel the greatest need for the speed and volume capabilities of an automatic analyzer have already invested in one or more automatic gamma counters, often complete with computer data processing. By purchasing that embodiment of the invention consisting of sampler, pump, mixer, incubator, any of several separators, and the test tube collection means, the laboratory can automate and greatly increase production at minimal expense. One of these analyzers could keep a number of their existing gamma counters busy.

Figure 7:
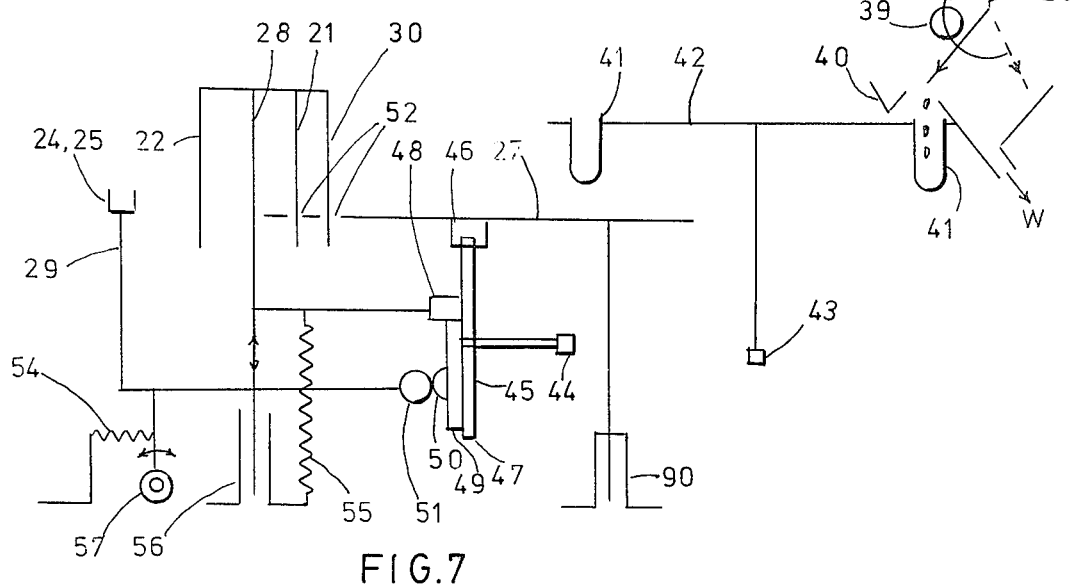
FIG. 7 is a diagram of some of the moving parts of the apparatus of FIG. 6.
Figure 6:
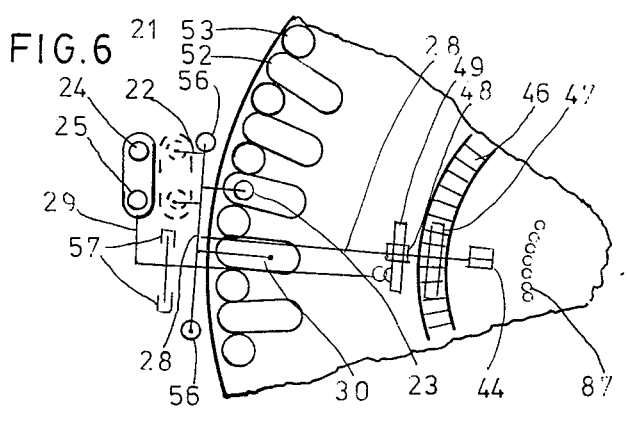
FIG. 6 is a top plan view of a portion of the sampler apparatus embodying a single driven cam for all timed motion functions.
Figure 8:
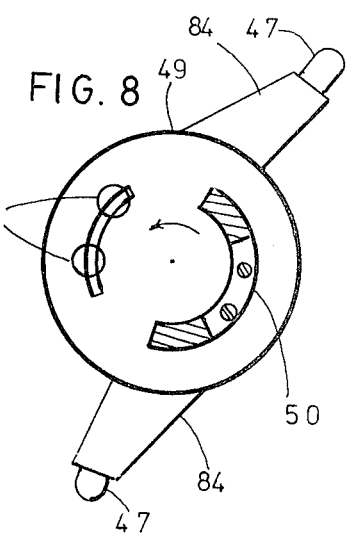
FIG. 8 is a front elevation of the three function cam of FIG. 6.

A novel sampler of simple and inexpensive construction is shown in partial plan view in FIG. 6 and a diagram of some of its parts in FIG. 7. Timing motor 44 drives 3 way cam 45 which powers all of the motions. The cam is shown in front elevation in FIG. 8 and side view in FIG. 9. In FIG. 8 cam rotation is counterclockwise as indicated by arrow. The two teeth 47 at the outermost periphery of the cam engage ring gear 46 on underside of sample support means 27 to provide two separate, intermittent steps of rotation of the disc 27 holding samples 23 for every continuous rotation of the motor. Every step advances the disc the same amount as assured by detent means in detent holes 87. The first step positions sample 23 in sample receptacle 53 directly beneath sample pipet 21. The second step positions elongate hole 52 in disc 27 directly beneath sample pipet 21. Movement of sample disc 27 always occurs when pipet 21 and reagent pipets 22 are in uppermost or clearance position shown in FIG. 1b so that pipet tips will not interfere with containers during their movement. The motion of sample pipet 21 and reagent pipets 22 and attached pipet support 28 is effected by portion 49 of cam 45 pushing against cam follower 28 attached to pipet support 28 and stretching tension spring 55. Two sliding sleeve bearings 56 guide and stabilize support 28 as it slides up and down therein. The angled leading edges of each of the two elevations 84 of cam portion 49 allows for a slower lifting of the pipets to the clearance position. They drop rapidly to one of the two alternating lower positions under action of spring 55 and sharp trailing edges of the cam. When sample pipet 21 is over a sample receptacle 23, pipet support 28 drops to the middle of sampling level shown in FIG. 1. Sample pipet tip 21 and reagent pipet tips 22 are immersed in sample 23 and ligand 24 and binding agent 25. This level is determined by level sensing finger 30 impinging upon the solid surface of sample support 27. It can be seen in FIG. 8 that lift to clearance position always occurs prior to sample motion. The wash or lowest pipet level seen in FIG. 1a occurs when pipet is over elongate hole 52 in disc 27 between two sample receptacles 53. Level sensing finger 30 is also over a hole 52 which it penetrates until it is stopped at the lowest level by cam follower 48 meeting lowest surface of pipet lifting part 49 of cam 45. In this position sample pipet 21 and reagent pipets 22 are immersed in wash liquid container 74. Alternatively, level sensing finger 30 may be dispensed with completely in this embodiment all three levels of pipets may be determined by three levels of cam part 49. When sample support means includes a detachable disc for holding samples, the sensing finger means can compensate for distortions of said disc. The to and fro motion of reagents 24 and 25 on reagent support 29 alternately aligns reagents beneath their pipets when they are about to descend to the sample level or moves them out of the way when the pipets are about to descend to the wash level. This motion is accomplished by projection 50 on face of cam 45. Sloping leading and trailing edges of the projection reduce velocity to avoid spillages. Some motion keeps reagents mixed. Reagent support 20 is pivotally fixed at its base by two bearings 57 which limit motion to rotation. Compression spring 54 forces cam follower 51 affixed to support 29 against face of cam 45 thereby causing support 29 to alternately swing in for sample position to supply reagents to reagent pipets and to swing out upon meeting projection 50 to allow reagent pipets to pass beside the reagents and into wash liquid container 74. The entire cam or cam and motor assembly may be replaced with another to alter timing relationships. The cam shown has adjustable and replaceable parts so that the ratio of sample time to wash time may be easily altered with clamp screws 58. Variable speed timing motors are available for adjustment of the sample per minute rate. Another embodiment of the sampler mechanism employs separate, but sequentially dependant means for pipet motion, sample motion, and reagent motion. This is shown in a partial plan view in FIG. 10 and a diagrammatic side view in FIG. 11. Time switch 85 controls the duration of sample and wash intervals. It activates pull solenoid 61 pulling down lever 63 pivotally supported at fulcrum 62. The other end of lever acting against tension spring 55 forces pipet support 28 upward. Pipet support 28 slides in the two sliding sleeve bearings 56. The motion of pipet support 28 may also be accomplished by the actuator disclosed in Blum, U.S. Pat. No. 3,877,226. Microswitch 64 is activated when pipets reach clearance level. This operates stepping motor 43, which drives sample support means 27 one increment, alternately presenting a sample receptacle 53 or an elongate hole 52 in the sample support to the sample pipet. Completion of the rotation step operates step microswitch 66, which deenergizes solenoid 61 allowing spring 55 to pull pipet support down to the other two levels as determined by level sensing finger 30. The third motion, the to and fro motion of the reagent support is provided by cam 65 beneath and rotating with, sample disc 27. Reagent support 29 is pivotally supported and stabilized at its base by two bearings 57. Tension spring 54 pulls cam follower 51 against cam 65. Projections of the cam push against cam follower 51 when they appear at wash cycle to rotate support 29 outwardly, moving reagents out of alignment with pipets 22 and allowing said pipets to pass beside reagents and into wash liquid container 74. Duration of the wash cycle and sample cycle are controlled by the timing switch 85 which will activate solenoid 61 for the next interval. Optical detector shown diagrammatically in FIG. 12 includes a fluid channel 69 with light transmitting walls, a light source 68 on one side and a light sensor 70 on the other side of the fluid channel so arranged that light must pass through the fluid channel to reach the light sensor. The entire assembly is protected by light shield 71 from ambient light. May include filter 86 to restrict spectral sensitivity of the detector. When channel contents contains materials which absorb sufficient light of the particular wavelength this is indicated by a change in output of the sensor. When the light absorbing agent is fluorescent, first filter 86 between source 68 and channel 69 may pass excitation wavelengths and second filter 86 between channel 69 and sensor 70 may pass emission wavelengths. Electrical connections can be so arranged that a signal is provided when light absorbing material appears in the channel, or when it disappears, or both. Some of the solid state light switches recently introduced incorporate most of these components. In some situations they may be employed as inexpensive optical detectors. Two position valve means shown in FIGS. 13, 14 and 15 employs power of solenoid coil 91 to pull down armature 92, shown midway between up and down position in FIG. 13. Armature extension bar 93, affixed to armature 92, is pulled down by solenoid action, stretching return spring 97 and compressing lower flexible tubing 26 against lower anvil 95, occluding said tubing as shown in FIG. 15. Anvil 15 is supported by tension springs 98 to limit force exerted on said tubing. Stops 94 limit upward spring travel. In this position fluid flow is limited to upper branch. In second position, solenoid is deenergized and tension of return spring 97 pulls bar 93 upward, compressing upper tubing 26 against upper anvil 96 which is fixed to housing 99. This action occludes upper tubing as shown in FIG. 14, limiting flow to lower branch. By this economical and simple means a single solenoid may become many two way valves. Chemical agents such as fluorescamine may be used to render fluorescent a ligand such as a peptide or a protein. This fluorochrome may be the labeling means. In which case, the corresponding label measuring means might be a flow through fluorometer of the type in current use in liquid charomatography.

While I have shown and described the preferred embodiments of my invention, it will be understood that the invention may be embodied otherwise than as herein specifically illustrated or described, and that certain changes in the form and arrangement of parts and in the specific manner of practicing the invention may be made without departing from the underlying idea or principles of this invention within the scope of the appended claims.

What is claimed is:

1. A continuous competitive binding analysis apparatus which comprises: means for dispensing, mixing, and incubating, in a fluid stream, a plurality of successive sample solution mixture segments (M), each of which comprises a mixture of (a) a sample possibly containing a ligand, (b) a solution of a known concentration of said ligand labeled with a measureable labeling means and (c) a solution of a binding agent reactable with said ligand; means for the introduction of alternate spacer segments (S); said dispensing means including (d) carrier means for containers for a series of said samples, (e) receptacle means mounted beneath the plane of said containers for providing spacer or wash liquid segments between liquid samples, (g) take off means moving alternately into and out of said containers and said receptacle means respectively, (h) vertical motion means to move said take off means to three levels, a first, uppermost clearance level above the top of said containers providing unobstructed movement of sample container carrier means to position successive samples at said take off means, a second, sampling level for withdrawing said liquid samples from said containers, and a third, lowermost level for withdrawing spacer liquid from said receptacle, wherein said take off means passes through an opening in said carrier means between said successive sample containers, (i) means to move said carrier in cooperation with said take off means movement to alternately position successive sample containers and openings between containers in line with vertical movement of said take off means; light absorbing means incorporated into either segment (M) or segment (S); optical detector means for detecting the presence or absence of light absorbing means within the fluid stream passing said detection means whereby spacer segment (S) is distinguished from sample mixture segment (M); fluid flow directing means activateable by said detector means for directing analytical processing of said mixture segment (M), said fluid directing means including a solenoid actuated, spring loaded member alternately occlusively compressing a first branch of one or more forked tubes by solenoid action in a first position and occlusively compressing the second branch by opposite spring action in the second position; separating means for separating said sample mixture (M), after incubation, into a first portion containing ligand which is unreacted with said binding agent, and a second portion containing ligand reacted with said binding agent, wherein said separating means includes an adsorbtion column packed with adsorbent which selectively adsorbs either ligand reacted with binding agent or ligand unreacted with binding agent; label measurement means for measuring seriatim one of said separated sample portions, wherein said label is a radioactive isotope and label measurement means includes a plurality of flow through radioactivity measuring means, multiple position valve means for conducting the fluid flow from said separation means seriatim to fluid channel means within the sensitive volumes of each of said radioactivity measurement means in turn for static radioactivity measurement, said multiple position valve operating means operable by signal from optical detector means disposed in the fluid pathway between said separating means and said valve, whereby appearance of spacer fluid segment isolates a separated portion of sample mixture in a channel in a radioactivity measurement means for static measurement while a next spacer fluid segment purges a next channel in a next measurement means prior to a next separated sample entering said next channel for static measurement of radioactivity; and uniformity correction means to correct differences in sensitivity of individual measurement means.

2. The invention of claim 1, wherein label measurement means for measuring seriatim one of said separated sample portions includes: means activateable by signal from said optical detector means for isolating seriatim one of said separated sample portions for label measurement; a fluid conduit for conducting said portions, positionable between a first position wherein fluid is conducted to one of a series of sample segment containers wherein the isolated sample segment will be stored for later measurement of label in off line label measurement means, and a second position wherein fluid stream is conducted to waste to discard spacer liquid segment (S) interspersed between separated sample mixture segments (M); drop diverting means to divert fluid to waste which does not fall directly into opening of said sample segment container; container moving means to move previously filled container out of alignment with, and an empty container into alignment with said first position of said positionable conduit for filling with next separated sample mixture segment.

3. The invention of claim 1, wherein said label is a radioactive isotope and label measurement means for measuring seriatim one of said separated sample portions includes an alternating two position fluid flow directing means activateable by signal from optical detector means for isolating seriatim one of said separated sample portions for radioactivity measurement in said measurement means, wherein said separated sample portion is conducted to liquid channel means within the sensitive volume of said measurement means in a first position and the following spacer liquid segment (S) is conducted to waste in a second position, whereby said sample portion is at rest within said volume while measurement of radioactivity is performed; including means for the last portion of the liquid segment (S) to flush out the sample portion at the conclusion of the measurement interval prior to the entrance of the next sample portion.

4. An automatic continuous competitive binding analysis apparatus which comprises: means for dispensing, mixing, and incubating, in a fluid stream, a plurality of successive sample solution mixture segment (M), each of which comprises a mixture of (a) a sample possibly containing a ligand, (b) a solution of a known concentration of said ligand labeled with a measureable labeling means, and (c) a solution of a binding agent reactable with said ligand; means for the introduction of alternate spacer segments (S); said dispensing means including (d) carrier means for containers for a series of said samples, (e) receptacle means mounted beneath the plane of said containers for providing spacer or wash liquid segments (S) between liquid samples, (g) take off means moving alternately into and out of said containers and said receptacle means respectively, (h) vertical motion means to move said take off means to one of three levels, a first, uppermost clearance level above the top of said containers providing unobstructed movement of sample container carrier means to position successive samples at said take off means, a second, sampling level for withdrawing said liquid samples from said containers, and a third, lowermost level for withdrawing spacer liquid from said receptacle, wherein said take off means passes through an opening in said carrier means between said successive sample containers, (i) means to move said carrier in cooperation with said take off means movement to alternately position successive sample containers and openings between containers in line with vertical movement of said take off means, (j) one or more reagent vessels for providing reagents to mix with sample, located in a plane above said receptacle means, (k) a reagent take off means for each reagent moving alternately into and out of said reagent vessels and said receptacle means, respectively for alternately withdrawing said reagents and said spacer liquid, (1) vertical motion means to move said reagent take off means to three levels, a first, uppermost level above the top of said reagent vessels providing for unobstructed to and fro motion of said vessels, a second, middle level for withdrawing said reagents, and a third, lowermost level for withdrawing spacer liquid from said receptacle means, (m) means to move said reagent vessels laterally in to and fro motion in cooperation with reagent take off means to alternately position said reagent containers firstly in line with descent of said reagent take off means for supplying reagent and secondly, positioning said reagent containers beside and out of the way of the descent of said reagent take off means to the lowest level for supplying spacer liquid; optical detector means for detecting the presence of light absorbing means within the fluid stream passing said detector means whereby spacer segment (S) is distinguished from sample mixture (M); electrical separation means for separating said sample mixture (M), after incubation, into a first liquid portion containing ligand which is uncombined with binding agent, and a second liquid portion containing ligand which is combined with binding agent using electrical force to move electrically charged fluid components across controlled porosity membranes including, (1) a first elongate fluid channel for passing said sample mixture (M) therethrough, (2) at least one other elongate fluid channel for passing at least one other fluid adjacent said first channel and separated therefrom by permeable membrane means, said membrane means of a porosity to further separation of said ligand combined with binding agent from ligand uncombined with binding agent, (3) electrical field means applied across said channels in a direction transverse to the direction of fluid flow to cause migration of certain charged fluid components from one said channel across said membrane means into another said channel and into a separate moving fluid stream; label measurement means for measuring seriatim one of said separated sample portions, wherein said label is a radioactive isotope and label measurement means includes a plurality of flow through radioactivity measuring means, multiple position valve means for conducting the fluid flow from said separation means seriatim to sample fluid channel means within the sensitive volumes of each of said radioactivity measurement means in turn for static radioactivity measurement, said multiple position valve operating means operable by signal from optical detector means disposed in the fluid pathway between said separating means and said valve, whereby appearance of spacer fluid segment isolates a separated portion of sample mixture in a channel in a radioactivity measurement means for static measurement while a next spacer fluid segment purges a next channel in a next measurement means prior to a next separated sample entering said next channel for static measurement of radioactivity; and uniformity correction means to correct differences in sensitivity of individual measurement means.

5. The invention of claim 4, wherein label measurement means for measuring seriatim one of said separated sample portions includes: means activateable by signal from said optical detector means for isolating seriatim one of said separated sample portions for label measurement; a fluid conduit for conducting said portions, positionable between a first position wherein fluid is conducted to one of a series of sample segment containers wherein the isolated sample segment will be stored for later measurement of label in off line label measurement means, and a second position wherein fluid stream is conducted to waste to discard spacer liquid segment (S) interspersed between separated sample mixture segments (M); container moving means to move previously filled container out of alignment with, and an empty container into alignment with said first position of said positionable conduit for filling with next separated sample mixture segment.

6. The invention of claim 4, wherein said label is a radioactive isotope and label measurement means for measuring seriatim one of said separated sample portions includes an alternating two position fluid flow directing means activateable by signal from optical detector means for isolating seriatim one of said separated sample portions for radioactivity measurement in said measurement means, wherein said separated sample portion is conducted to liquid channel means within the sensitive volume of said measurement means in a first position and the following spacer liquid segment (S) is conducted to waste in a second position, whereby said sample portion is at rest within said volume while measurement of radioactivity is performed; including means for the last portion of the liquid segment (S) to flush out the sample portion at the conclusion of the measurement interval prior to the entrance of the next sample portion.

7. Apparatus of claim 4, wherein light absorbing means comprises a light absorbing, water soluble material essentially nonreactable with constituents, forces and other materials it contacts within the apparatus and having a size large enough to inhibit its movement through the pores of said membrane means.

8. Apparatus of claim 4, wherein the light absorbing means comprises a light absorbing material combined with said binding agent to form a light absorbing, water soluble molecule of molecular size very large relative to ligand size and reactable with said ligand and having a size large enought to inhibit its movement through the pores of said membrane means.

9. Apparatus of claim 4, wherein labels means is a fluorochrome, which further comprises fluorescence measuring means.

10. Apparatus of claim 4, wherein label means is an enzyme, which further comprises enzyme measuring means.

11. Apparatus of claim 1, wherein label means is an enzyme, which further comprises enzyme measuring means.

12. Apparatus of claim 1, wherein label means is a fluorochrome, which further comprises fluorescence measuring means.

13. The apparatus of claim 1, wherein said separation of bound from unbound ligand and the separation of one sample from another is enhanced by said alternating two position fluid flow directing means activated by said optical detector means which, in first position, directs said sample mixture segment (M) onto said column while air bubbles are vented from column and, in second position, directs spacer liquid segment (S) to waste and directs higher volumn eluting fluid flow from eluting fluid means through said column.

14. Apparatus of claim 1, which further comprises: one or more reagent containers for providing reagents to mix with sample, located in a plane above said receptacle means; a reagent take off means for each reagent moving alternately into and out of said reagent containers and sid receptacle means, respectively, for alternately withdrawing said reagents and said spacer liquid; vertical motion means to move said reagent take off means to three levels, a first, uppermost, level above the top of said reagent containers providing unobstructed to and fro motion of said containers, a second middle level for withdrawing said reagents, and a third, lowermost level for withdrawing spacer liquid from said receptacle means; means to move said reagent containers laterally to and fro in cooperation with said reagent take off means motion to alternately position said reagent containers firstly in line with descent of said reagent take off means for supplying reagent and, secondly, positioning said reagent containers beside and out of the way of descent of said take off means to the lowest level for supplying spacer liquid.

15. Apparatus of claim 14, wherein all take off means movement is provided by means driven by electric motor means; carrier means movement is provided by means driven by said motor means; reagent container movement is provided by means driven by said motor means.

16. The invention of claim 4, wherein electrical separation means further comprises: first and second members, each having a surface with groove means therein, said groove means having fluid inlet and outlet means; electrode means in said groove means; an inner member having slot means, said slot means having fluid inlet and outlet means; mounting means for mounting said first and said inner members in confronting face to face relation with said groove means in registry with said slot means, and for mounting said second and said inner members in confronting face to face relation with said groove means in registry with said slot means at another face of said inner member; permeable membrane means interposed between said first and said inner members and permeable membrane means interposed between said second and said inner members, so as to form three fluid channels with common permeable walls between said channels; and means for applying electrical potential between said electrode means.

17. Apparatus of claim 16, wherein no inner member is provided; said first member is mounted in confronting face to face relation with said second member with said groove means in registry with one another; and permeable membrane means interposed between said members so as to form two fluid channels with a common permeable wall therebetween.

18. Apparatus of claim 16, which further comprises: a plurality of inner members with slot means mounted in registry; a plurality of permeable membrane means interposed between individual inner members and between outermost of said inner members and said first and second members so as to form a plurality of fluid channels with common walls therebetween.

19. Apparatus of claim 16, wherein said groove means is formed by a combination of a separate slotted member applied to a flat member.

20. Apparatus of claim 16, wherein the distance between channels is short relative to the length of said channels, providing a short exit path for migrating molecules and a relatively long exposure to the electrical force.

21. A method of continuous competitive binding analysis, which comprises: dispensing, mixing and incubating, in a flowing stream, a plurality of successive sample solution mixtures (M), each of which comprises a mixture of a sample possibly containing a ligand, a solution of known concentration of said ligand labeled with a measureable labeling means and a solution of a binding agent reactable with said ligand; introducing alternate spacer liquid segments (S) between each of said successive sample solution mixture segments (M); separating by electrical separation means said successive sample solution mixture (M), after incubation and while continuously flowing and retaining said spacer liquid segments (S), into a first liquid portion in one stream containing ligand combined with binding agent and a second liquid portion in another stream containing uncombined ligand including the steps of:

(1) Passing said succession of sample solution mixtures through a first elongate fluid channel;

(2) Passing at least one other fluig through at least one other elongate fluid channel adjacent said first channel and separated therefrom by permeable membrane means;

(3) Applying an electrical field means across said channels in a direction transverse to the direction of fluid flow to cause migration of certain charged fluid components from one channel across said membrane means into another said channel and into a separate moving fluid stream;

(4) Providing a short exit path for electrically migrating components and a relatively long path for exposure to the electrical field;

passing at least one of said separated sample streams into label measurement means and measurement seriatim of the labeled ligand in said separated portions wherein said label is a radioactive isotope and label measurement means includes a plurality of flow through radioactivity measuring means, multiple position valve means for conducting the fluid flow from said separation means seriatim to sample fluid channel means within the sensitive volumes of each of said radioactivity measurement means in turn for static radioactivity measurement; operating said multiple position valve means by signal from optical detector means disposed in the fluid pathway between said separating means and said valve, whereby appearance of spacer fluid segment isolates a separated portion of sample mixture in a channel in a radioactivity measurement means for static measurement while a next spacer fluid segment purges a next channel in a next measurement means prior to a next separated sample entering said next channel for static measurement of radioactivity.

22. The method of claim 21, wherein label measurement means is a single flow through radioactivity measuring means and the method includes: isolating each separated sample and measuring radioactivity seriatim by operating 2 position fluid directing means alternately to a first position which conducts a separated portion of a sample mixture segment (M) into a fluid channel within the sensitive volume of a radioactivity measurements means; next, upon sensing completion of passage of said segment (M) by optical detector means, operating said fluid directing means to a second position thereby conducting spacer liquid segment (S) to waste, while radioactivity measurement of preceding sample segment isolated in said channel is begun; returning said fluid directing means to said first position upon completion of the measurement; next flushing the already measured segment (M) to waste with the balance of the spacer liquid segment (S); next filling said channel with the following segment (M) to begin the next cycle.

23. The method of claim 22, wherein operation of 2 position fluid directing means comprises selectively directing the flow of fluid from a channel into one of two branches including the steps of: occlusively compressing a first branch by solenoid action on a compressing member in a first position to direct fluid flow through the second branch; occlusively compressing said second branch by opposite spring action on said member wherein solenoid is not actuated in a second position to direct fluid flow through said first branch.

24. The method of claim 21, wherein separated portions of mixture (M) are isolated for subsequent label measurement by means of optical detector means actuating container filling means; successively dispensing to one of a series of liquid sample containers the said separated portion of one mixture segment (M); conducting the next fluid segment of the stream to waste thereby discarding spacer segment (S) interspersed between samples; while another in a series of empty sample containers is presented to filling means to be filled by next appearing mixture segment (M) upon signal from said optical detector means.

25. The method of claim 21, including adjusting net electrical charge of certain fluid components by pH adjustment of said fluid to control separation by electrical field means.

26. The method of claim 21, which further comprises the steps of mixing at least one of the fluid streams leaving a first electrical separation means with pH adjusting fluid to alter the net electrical charge of certain components, and passing said mixture through another electrical separation process to provide a further separation.

27. The method of claim 21, which further comprises the steps of mixing at least one of the fluid streams leaving a first electrical separation means with another reagent to alter the properties of certain components, and passing said mixture through another electrical separation process to provide a further separation of components.

28. The method of claim 21, which includes combining said binding agent with light absorbing material of such large size relative to the pore size of said permeable membrane means as to inhibit passage of ligand bound to said material through said permeable membrane means.

29. The method of claim 21, which includes combining said binding agent with material of such large size relative to the pore size of said permeable membrane means at to inhibit passage of ligand bound to said material through said permeable membrane means.

30. A method of continuous competitive binding analysis, which comprises: dispensing, mixing and incubating, in a flowing stream, a plurality of successive sample solution mixtures (M). each of which comprises a mixture of a sample possibly containing a ligand, a solution of known concentration of said ligand labeled with a measurable labeling means and a solution of a binding agent reactable with said ligand; introducing alternate spacer liquid segments (S) between each of said successive sample solution mixture segments (M); incorporating light absorbing material means into either of said segments (M) or (S) for actuating optical detector means; separating bound ligand from unbound ligand in an adsorbtion column by the alternating steps of firstly passing a flow of said sample mixture (M) onto said column, and secondly diverting flow of said spacer liquid segment (S) to waste while passing an eluting liquid onto said column, wherein timing of said steps is controlled by said optical detector means, wherein label is a radioactive isotope and label measuring means is a plurality of radioactivity measuring means each of which has a fluid channel within its sensitive volume, having outlet means connected to waste and inlet means connected to separate outlets of a multioutlet valve means which further comprises: conducting the fluid stream from said separating means containing one of said separated sample mixture portions (M), interspersed with spacer liquid segments (S), through optical detector means to the inlet of said multiple outlet valve means; employing the signal means from said detector means to operate said valve means so as to entrap a sample mixture segment within one of said channels for static radioactivity measurement while the following spacer segment (S) flows into a second channel washing out trapped sample from an earlier cycle; continuing this flow until a second sample mixture is within said second channel; again actuating said valve means and beginning radioactivity measurement on sample now entrapped in said second channel; continuing the process of washing out each successive channel with spacer liquid and then entrapping the next sample segment and measuring its radioactivity.

31. The method of claim 30 employing a single radioactivity measurement means which further comprises: isolating each separated sample and measuring radioactivity seriatim by said 2 position fluid directing method alternately to a first position which conducts a separated portion of a sample mixture segment (M) into a fluid channel within the sensitive volume of a radioactivity measurement means; next, upon sensing completion of passage of said segment (M) by optical detector means, operating said fluid directing means to a second position thereby conducting spacer liquid segment (S) to waste, while radioactivity measurement of preceding sample segment isolated in said channel is begun; returning said fluid directing means to said first position upon completion of the measurement; next flushing the already measured segment (M) to waste with the balance of the spacer liquid segment (S); next filling said channel with the following segment (M) to begin the next cycle.

32. The method of claim 31, wherein separated portions of mixture (M) are isolated for subsequent label measurement by means of said optical detector signal actuating containing filling means; successively dispensing to one of a series of liquid sample containers the said separated portion of one mixture segment (M); conducting the next fluid segment of the stream to waste thereby discarding spacer segment (S) interspersed between samples, while another in a series of empty sample containers is presented to filling means to be filled by next appearing mixture segment (M) upon signal from said optical detector means.

33. The method of claim 31, wherein alternating fluid flow steps comprises directing the flow of fluid from a channel into one of two branches by occlusively compressing a first branch by solenoid action on a compressing member in a first position to direct fluid flow through the second branch, and occlusively compressing said second branch by opposite spring action on said member when solenoid is inactive in a second position to alternately direct fluid flow through said first branch.

34. The method of claim 31, wherein the dispensing of said alternating liquid segments (M) and (S) comprises the repetition of the sequential steps: (1) immersing tip of sample take off means into one of a successive series of liquid sample container means for providing liquid sample and also immersing tips of one or more reagent take off means in one or more reagent container means for providing liquid reagent; (2) moving said sample take off means and said reagent take off means essentially vertically to an uppermost level sufficiently above said container means to provide clearance for their lateral movement; (3) moving said container means laterally out of the vertical motion pathway of said take off means; (4) moving said take off means down, essentially vertically to immerse their tips in spacer liquid receptacle means for providing said spacer liquid segment at a plane below the level of said containers; (5) raising all take off means, essentially vertically to said uppermost level; (6) moving reagent container means and another liquid sample container means laterally into the vertical pathways of their respective take off means.

35. The method of claim 30, including incorporating gas bubbles into certain fluid streams to reduce carry-over between successive samples.

36. The method of claim 21, wherein the dispensing of said alternating liquid segments (M) and (S) comprises the repetition of the sequential steps: (1) immersing tip of sample take off means into one of a successive series of liquid sample container means for providing liquid sample and also immersing tips of one or more reagent take off means in one or more reagent container means for providing liquid reagent; (2) moving said sample take off means and said reagent take off means essentially vertically to an uppermost level sufficiently above said container means to provide clearance for their lateral movement; (3) moving said container means laterally out of the vertical motion pathway of said take off means; (4) moving said take off means down, essentially vertically to immerse their tips in spacer liquid receptacle means for providing said spacer liquid segment at a plane below the level of said containers; (5) raising all take off means, essentially vertically to said uppermost level; (6) moving reagent container means and another liquid sample container means laterally into the vertical pathways of their respective take off means.

37. The method of claim 21, including incorporating gas bubbles into certain fluid streams to reduce carry-over between samples.

38. The method of claim 21, including using a membrane of a pore size to selectively inhibit the movement of the larger combined ligand therethrough while not inhibiting the movement of the smaller uncombined ligand.

39. A continuous competitive binding analysis apparatus which comprises: means for dispensing, mixing, and incubating, in a fluid stream, a plurality of successive sample solution mixture segments (M), each of which comprises a mixture of (a) a sample possibly containing a ligand, (b) a solution of a known concentration of said ligand labeled with a measurable labeling means and (c) a solution of a binding agent reactable with said ligand; means for the introduction of alternate spacer segments (S); light absorbing means incorporated into either segment (M) or segment (S); optical detector means for detecting the presence or absence of light absorbing means within the fluid stream passing said detection means whereby spacer segment (S) is distinguished from sample mixture segment (M); fluid flow directing means activateable by said detector means for directing analytical processing of said mixture segment (M); separating means for separating said sample mixture (M), after incubation, into a first portion containing ligand which is unreacted with said binding agent, and a second portion containing ligand reacted with said binding agent, wherein said separating means includes an adsorbtion column packed with adsorbent which selectively adsorbs either ligand reacted with binding agent or ligand unreacted with binding agent; label measurement means for measuring seriatim one of said separated sample portions, wherein said label is a radioactive isotope and label measurement means includes a plurality of flow through radioactivity measuring means, multiple position valve means for conducting the fluid flow from said separation means seriatim to sample fluid channel means within the sensitive volumes of each of said radioactivity measurement means in turn for static radioactivity measurement, said multiple position valve operating means operable by signal from optical detector means disposed in the fluid pathway between said separating means and said valve, whereby appearance of spacer fluid segment isolates a separated portion of sample mixture in a channel in a radioactivity measurement means for static measurement while a next spacer fluid segment purges a next channel in a next measurement means prior to a next separated sample entering said next channel for static measurement of radioactivity; and uniformity correction means to correct differences in sensitivity of individual measurement means.

40. The invention of claim 39, wherein label measurement means for measuring seriatim one of said separated sample portions includes; means activateable by signal from said optical detector means for isolating seriatim one of said separated sample portions for label measurement; a fluid conduit for conducting said portions, positionable between a first position wherein fluid is conducted to one of a series of sample segment containers wherein the isolated sample segment will be stored for later measurement of label in off line label measurement means, and a second position wherein fluid stream is conducted to waste the discard spacer liquid segment (S) interspersed between separated sample mixture segments (M); drop diverting means to divert fluid to waste which does not fall directly into opening of said sample segment container; container moving means to move previously filled container out of alignment with, and an empty container into alignment with said first position of said positionable conduit for filling with next separated sample mixture segment.

41. The invention of claim 39, wherein said label is a radioactive isotope and label measurement means for measuring seriatim one of said separated sample portions includes an alternating two position fluid flow directing means activateable by signal from optical detector means for isolating seriatim one of said separated sample portions for radioactivity measurement in said measurement means, wherein said separated sample portion is conducted to liquid channel means within the sensitive volume of said measurement means in a first position and the following spacer liquid segment (S) is conducted to waste in a second position, whereby said sample portion is at rest within said volume while measurement of radioactivity is performed; including means for the last portion of the liquid segment (S) to flush out the sample portion at the conclusion of the measurement interval prior to the entrance of the next sample portion.

42. The apparatus of claim 39, wherein said separation of bound from unbound ligand and the separation of one sample from another is enhanced by said alternating two position fluid flow directing means activated by said optical detector means which, in first position, directs said sample mixture segment (M) onto said column while air bubbles are vented from column and, in second position, directs spacer liquid segment (S) to waste and directs high volume eluting fluid flow from eluting fluid means through said column.

43. Apparatus of claim 39, which further comprises: one or more reagent containers for providing reagents to mix with sample, located in a plane above said receptacle means; a reagent take off means for each reagent moving alternatively into and out of said reagent containers and said receptacle means, respectively, for alternately withdrawing said reagents and said spacer liquid; vertical motion means to move said reagent take off means to three levels, a first, uppermost, level above the top of said reagent containers providing unobstructed to and fro motion of said containers, a second middle level for withdrawing said reagents, and a third, lowermost level for withdrawing spacer liquid from said receptacle means; means to move said reagent containers laterally to and fro in cooperation with said reagent take off means motion to alternately position said reagent containers firstly in line with descent of said reagent take off means for supplying reagent and, secondly, positioning said reagent containers beside and out of the way of descent of said take off means to the lowwest level for supplying spacer liquid.

44. Apparatus of claim 43, wherein all take off means movement is provided by means driven by electric motor means; carrier means movement is provided by means driven by said motor means; reagent container movement is provided by means driven by said motor means.

45. An automatic continuous competitive binding analysis apparatus which comprises: means for dispensing, mixing, and incubating, in a fluid stream, a plurality of successive sample solution mixture segments (M), each of which comprises a mixture of (a) a sample possibly containing a ligand, (b) a solution of a known concentration of said ligand labeled with a measureable labeling means, and (c) a solution of a binding agent reactable with said ligand; means for the introduction of alternate spacer segments (S); light absorbing means incorporated into either segment (M) or segment (S); optical detector means for detecting the presence of light absorbing means within the fluid stream passing said detector means whereby spacer segment (S) is distinguished from sample mixture segment (M); electrical separation means for separating said sample mixture (M), after incubation, into a first liquid portion containing ligand which is uncombined with binding agent, and a second liquid portion containing ligand which is combined with binding agent using electrical force to move electrically charged fluid components across controlled porosity membranes including, (1) a first elongate fluid channel for passing said sample mixture (M) therethrough, (2) at least one other elongate fluid channel for passing at least one other fluid adjacent said first channel and separated therefrom by permeable membrane means, said membrane means of a porosity to further separation of said ligand combined with binding agent from ligand uncombined with binding agent, (3) electrical field means applied across said channels in a direction transverse to the direction of fluid flow to cause migration of certain charged fluid components from one said channel across said membrane means into another said channel and into a separate moving fluid stream; label measurement means for measuring seriatim one of said separated sample portions, wherein said label is a radioactive isotope and label measurement means includes a plurality of flow through radioactivity measuring means, multiple position valve means for conducting the fluid flow from said separation means seriatim to fluid channel means within the sensitive volumes of each of said radioactivity measurement means in turn for static radioactivity measurement, said multiple position valve operating means operable by signal from said optical detector means disposed in the fluid pathway between said separating means and said valve, whereby appearance of spacer fluid segment isolates a separated portion of sample mixture in a channel in a radioactivity measurement means for static measurement while a next spacer fluid segment purges a next channel in a next measurement means prior to a next separated sample entering said next channel for static measurement of radioactivity; and uniformity correction means to correct differences in sensitivity of individual measurement means.

46. The invention of claim 45, wherein label measurement means for measuring seriatim one of said separated sample portions includes: means activateable by signal from said optical detector means for isolating seriatim one of said separated sample portions for label measurement; a fluid conduit for conducting said portions, positionable between a first position wherein fluid is conducted to one of a series of sample segment containers wherein the isolated sample segment will be stored for later measurement of label in off line label measurement means, and a second position wherein fluid stream is conducted to waste to discard spacer liquid segment (S) interspersed between separated sample mixture segments (M); container moving means to move previously filled container out of alignment with, and an empty container into alignment with said first position of said positionable conduit for filling with next separated sample mixture segment.

47. The invention of claim 45, wherein said label is a radioactive isotope and label measurement means for measuring seriatim one of said separated sample portions includes an alternating two position fluid flow directing means activateable by signal from optical detector means for isolating seriatim one of said separated sample portions for radioactivity measurement in said measurement means, wherein said separated sample portion is conducted to liquid channel means within the sensitive volume of said measurement means in a first position and the following spacer liquid segment (S) is conducted to waste in a second position, whereby said sample portion is at rest within said volume while measurement of radioactivity is performed; including means for the last portion of the liquid segment (S) to flush out the sample portion at the conclusion of the measurement interval prior to the entrance of the next sample portion.

48. Apparatus of claim 45, wherein light absorbing means comprises a light absorbing, water soluble material essentially nonreactable with constituents, forces and other materials it contacts within the apparatus and having a size large enough to inhibit its movement through the pores of said membrane means.

49. Apparatus of claim 45, wherein the light absorbing means comprises a light absorbing material combined with said binding agent to form a light absorbing, water soluble molecule of molecular size very large relative to ligand size and reactable with said ligand and having a size large enough to inhibit its movement through the pores of said membrane means.

50. Apparatus of claim 45, wherein label means is a fluorochrome, which further comprises fluorescence measuring means.

51. Apparatus of claim 45, wherein label means is an enzyme, which further comprises enzyme measuring means.

52. The invention of claim 45, wherein electrical separation means further comprises: first and second members, each having a surface with groove means therein, said groove means having fluid inlet and outlet means; electrode means in said groove means; an inner member having slot means, said slot means having fluid inlet and outlet means; mounting means for mounting said first and said inner members in confronting face to face relation with said groove means in registry with said slot means, and for mounting said second and said inner members in confronting face to face relation with said groove means in registry with said slot means at another face of said inner member; permeable membrane means interposed between said first and said inner members and permeable membrane means interposed between said second and said inner members, so as to form three fluid channels with common permeable walls between said channels; and means for applying electrical potential between said electrode means.

53. Apparatus of claim 52, wherein no inner member is provided; said first member is mounted in confronting face to face relation with said second member with said groove means in registry with one another; and permeable membrane means interposed between said members so as to form two fluid channels with a common permeable wall therebetween.

54. Apparatus of claim 52, which further comprises: a plurality of inner members with slot means mounted in registry; a plurality of permeable membrane means interposed between individual inner members and between outermost of said inner members and said first and second members so as to form a plurality of fluid channels with common walls therebetween.

55. Apparatus of claim 52, wherein said groove means is formed by a combination of a separate slotted member applied to a flat member.

56. Apparatus of claim 52, wherein the distance between channels is short relative to the length of said channels, providing a short exit path for migrating molecules and a relatively long exposure to the electrical force.

* * * * *